United States Patent
Takase et al.

(10) Patent No.: US 6,462,195 B1
(45) Date of Patent: Oct. 8, 2002

(54) METHODS FOR HIGHLY SELECTIVELY O-ALKYLATING AMIDE COMPOUNDS WITH THE USE OF COPPER SALTS

(75) Inventors: Mitsuru Takase, Niigata (JP);
Yasuyuki Miyazawa, Niigata (JP);
Shiro Tsubokura, Niigata (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/622,906

(22) PCT Filed: Mar. 4, 1999

(86) PCT No.: PCT/JP99/01053
§ 371 (c)(1),
(2), (4) Date: Sep. 5, 2000

(87) PCT Pub. No.: WO99/44969
PCT Pub. Date: Sep. 10, 1999

(30) Foreign Application Priority Data

Mar. 6, 1998 (JP) ............................................ 10-073099

(51) Int. Cl.[7] ............................................ C07D 239/52
(52) U.S. Cl. ...................................... 544/314; 544/332
(58) Field of Search ................................ 544/314, 332

(56) References Cited

U.S. PATENT DOCUMENTS 3,965,174 * 6/1976 Malz, Jr. et al. ......... 260/561 H

FOREIGN PATENT DOCUMENTS

| EP | 0 278 595 | 8/1988 |
|----|-----------|--------|
| EP | 0 472 224 | 2/1992 |
| JP | 63-216848 | 9/1988 |
| JP | 279330 | 10/1993 |
| WO | 97/01538 | 1/1997 |

OTHER PUBLICATIONS

Derwent Acc No. 1993–374581, DWPI Abstract of JP 05–279330 A, Oct. 1993.*
Corbridge, Phosphorous—An Outline of its Chemistry, Biochemistry and Uses (Fifth Edition), pp. 124–130, 1995.*
Material Safety Data Sheet for Phosphine, Voltaix, Inc., 1994.*
Hopkins et al.; Alkylations of Heterocyclic Ambident Anions. II. Alkylation of 2–Pyridone Salts; J. Org. Chem. pp. 4040–4044 vol. 32, (1967).

* cited by examiner

Primary Examiner—Deepak R. Rao
(74) Attorney, Agent, or Firm—Jacobson Holman, PLLC

(57) ABSTRACT

Compounds having one or more structures represented by general formula (I) as partial structure thereof, which are typified by pyrimidone and pyridone compounds, have two or more reaction sites in alkylation reactions. Accordingly, there is no process for producing O-alkylated products of these compounds at a high selectivity or such processes, if any, are applicable exclusively to those having limited structures. A process for selectivity O-alkylating such a compound as described above by converting it into the copper salt by using a monovalent copper compound such as copper suboxide and then reacting it with an alkylating agent having a leaving group in the presence of a phosphorus compound such as a phosphite. Pyrimidyloxy derivatives or pyridyloxy derivatives obtained by this reaction is useful as intermediates of pesticides or drugs.

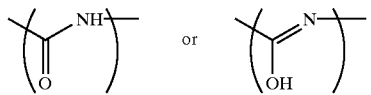

4 Claims, No Drawings

METHODS FOR HIGHLY SELECTIVELY O-ALKYLATING AMIDE COMPOUNDS WITH THE USE OF COPPER SALTS

This application is a 371 of PCT/JP99/01053 filed Mar. 4, 1999.

FIELD OF INVENTION

The present invention relates to methods for selectively O-alkylating chain or cyclic compounds having CONH groups or enol structures thereof in the molecules. Particularly it relates to methods suitable for preparing pyrimidyloxy or pyridyloxy derivatives, which are compounds useful as intermediates for agrochemicals and medicines, from pyrimidone or pyridone derivatives efficiently and highly selectively in high yields.

BACKGROUND ART

It is known that, when a chain or cyclic compound having one or more CONH groups or enol structures thereof as partial structures in the molecule is alkylated in a basic condition, N-alkyl compounds are produced in preference. Because of this, to obtain O-alkyll compounds selectively, for example, a carbonyl group was halogenated and then a substitution reaction was carried out with a corresponding alcohol in the presence of a base, or in the case of urea structure an isothiourea was synthesized from a corresponding thiourea and a substitution reaction was carried out with a corresponding alcohol. In other words, it was necessary to synthesize a halogenated compound or an isothiourea. There has been a problem that the above methods have applicable limits depending on substrates used.

Meanwhile, pyridyloxy or pyrimidyloxy derivatives are important as intermediates for agrochemicals, medicines and the like. For example, a series of compounds relating to them and their production processes are disclosed in EP 0472 224. However, when pyridyloxy or pyrimidyloxy derivatives are produced by the alkylation reactions of pyridone or pyrimidone compounds, byproducts unusable as target compounds are produced by N-alkylation reactions. Therefore the said processes have not been satisfactory economically.

In addition, J. Org. Chem. 32 4040 (1967) and Japanese Patent Laid-open No. Sho 63-216848 describe examples of preparing pyridyloxy derivatives and pyrimidyloxy derivatives by alkylation reactions of pyridone or pyrimidone with the use of alkali metal salts or silver salts. They have not been satisfactory as industrial production processes because of a large amount of N-alkylated byproducts produced other than target compounds or use of expensive silver salts.

In WO 97/01538 processes for the preparation of pyridyloxy derivatives are disclosed, but are limited to alkylation reactions of pyridones having a substituent at the position of 6.

As described above, in conventional technology, it is necessary to synthesize halogenated compounds or isothioureas, and there have been a problem of applicable limits depending on substrates used. Besides satisfactory results have not been accomplished, due to unnecessary byproducts produced when pyrimidone or pyridone compounds used as starting materials are changed to salts, such as alkali metal salts or silver salts, to react with various alkylating agents.

DISCLOSURE OF THE INVENTION

This invention is to provide economically advantageous methods that a chain or cyclic compound having one or more CONH groups or enol structures thereof as partial structures in the molecule, whose representatives are pyrimidone or pyridone compounds, is O-alkyllated highly selectively by a novel method to give a target compound selectively in high yield or very efficiently.

This invention relates to selective O-alkyllation methods characterized in that, in an O-alkyllation reaction of a chain or cyclic compound having one or more structures represented by Formula (I)

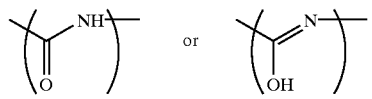

as partial structures, with Compound RL having a leaving group (wherein R is optionally substituted alkyl, optionally substituted allyl or optionally substituted aralkyl, and L is a leaving group), a monovalent copper salt derived from the said chain or cyclic compound is reacted in the presence of a phosphorus compound represented by Formula (II)

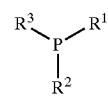

(wherein $R^1$, $R^2$ and $R^3$ are, each same or different, hydrogen, alkyl, aryl, aralkyl, alkoxy, aryloxy or aralkyloxy).

The present invention also relates to methods for selectively O-alkyllating pyrimidone, pyridone or triazine compounds of which the cyclic compounds having one or more structures represented by Formula (I) as partial structures are represented by Formula (III)

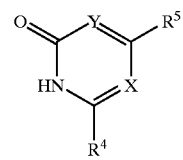

(wherein X and Y are each independently CH or N; $R^4$ is hydrogen, lower alkyl, haloalkyl or lower alkoxy; and $R^5$ is hydrogen, lower alkyl or trifluoromethyl). This invention also relates to selective O-alkyllation methods characterized in that the compound having a leaving group is represented by Formula (IV)

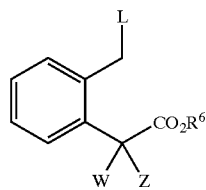

(wherein L is a leaving group; $R^6$ is lower alkyl; and W and Z are both hydrogen or become one to form =O, =NOCH$_3$ or =CHOCH$_3$), or by Formula (V)

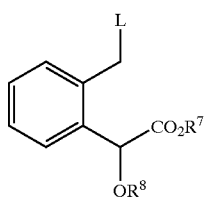

(wherein R[7] and R[8] are, same or different, chain or branched lower alkyl, haloalkyl, cycloalkyl or aralkyl; and L is as defined above). The present invention also relates to methods for selectively O-alkyllation compounds where Formula (III) is represented by

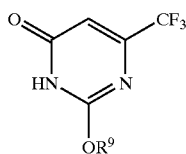

(wherein R[9] is lower alkyl).

The compounds used as starting materials in the present invention and having one or more structures represented by Formula (I) as partial structures in the molecules, that is, compounds having one or more CONH groups or enol structures thereof as partial structures in the molecules, are not particularly restricted if they have structures able to form copper salts with monovalent copper compounds such as copper (I) oxide. Concrete examples include compounds having basic skeletons such as those shown below:

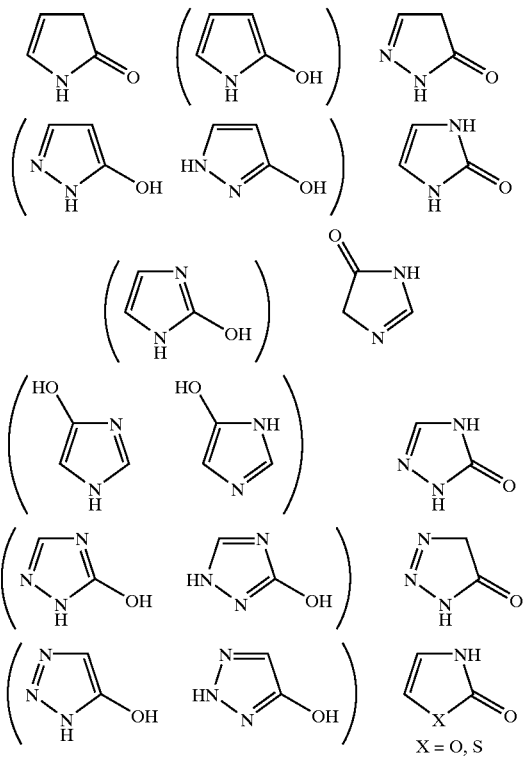

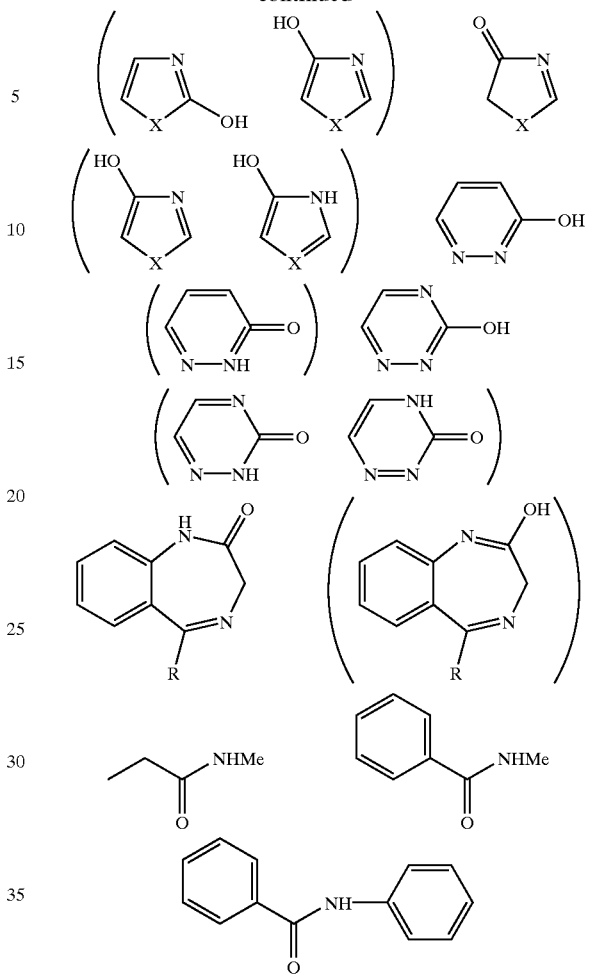

Compounds shown in brackets are tautomers.

Particularly pyrimidyloxy compounds, pyridyloxy compounds or triazinyloxy compounds, which are useful as intermediates for agrochemicals or medicines, can be produced if the methods of the present invention are applied to pyrimidone, pyridone or triazine compounds represented by Formula (III)

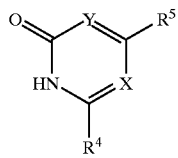

(wherein X and Y are each independently CH or N; R[4] is hydrogen, lower alkyl, haloalkyl or lower alkoxy; and R[5] is hydrogen, lower alkyl or trifluoromethyl),. Concrete examples include compounds shown in the following:

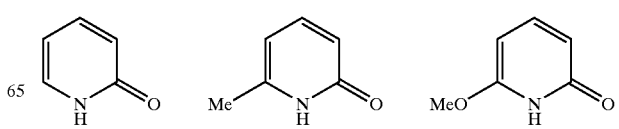

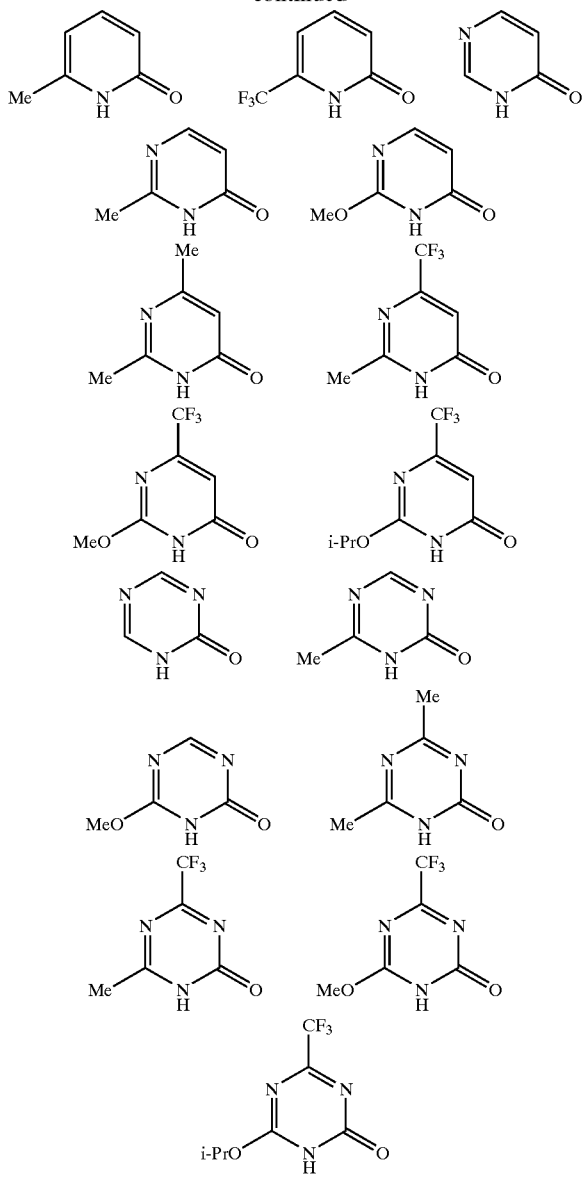

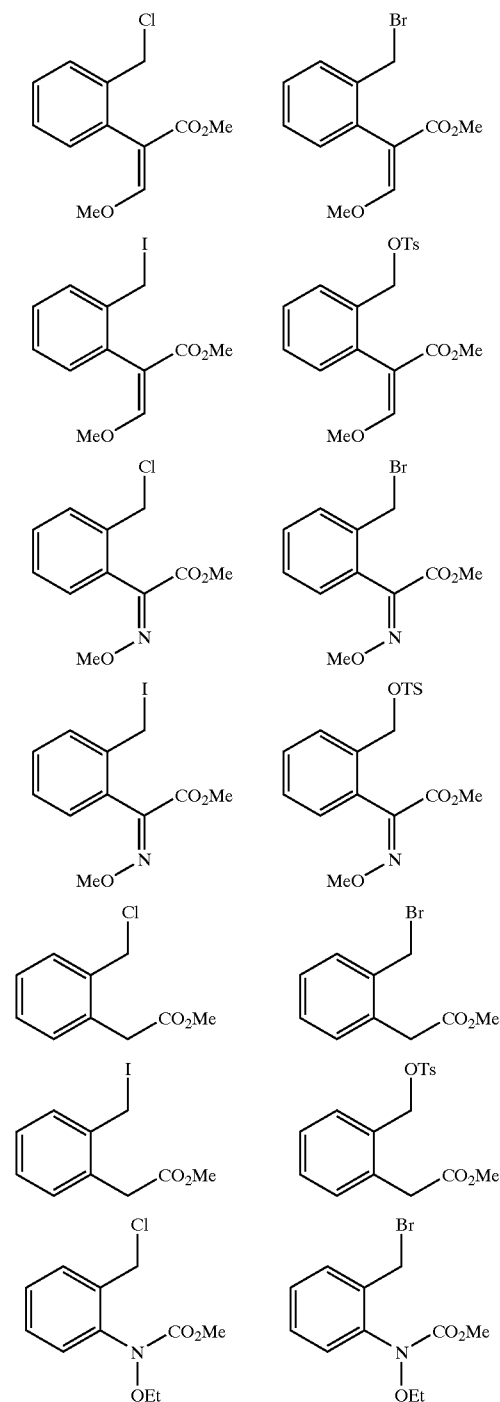

the structure required for a target compound of pyrimidyloxy or pyridyloxy derivative, and is not particularly restricted. It represents optionally substituted alkyl, allyl or aralkyl depending on the purpose. Concrete examples include methyl, ethyl, isopropyl, allyl and benzyl. Among them, compounds represented by Formulae (IV) and (V) are particularly useful because produced compounds become intermediates for agrochemicals and medicines when selective O-alkyllation reactions are carried out using them. Concrete examples of compounds represented by Formulae (IV) and (V) include those shown in the following:

In the present invention, general preparation methods to derive a monovalent copper salt from a chain or cyclic compound having one or more structures represented by Formula (I) as partial structures include, for example, a dehalogenating alkali-metal reaction of an alkali metal salt, such as lithium and potassium, of the aforementioned pyrimidone or pyridone compound with monovalent halogenated copper, such as monovalent copper chloride, or synthesis by reacting monovalent copper cyanide with the aforementioned pyrimidone or pyridone compound. Synthesis by a direct dehydration reaction of the said pyrimidone or pyridone compound with the use of copper(I) oxide ($Cu_2O$) is however easiest, and gives a monovalent copper salt with high purity. Besides, it gives extremely good results to the following alkylation reaction.

Compound RL having a leaving group, which is used in the reaction with a copper salt in the present invention, has Leaving Group L. L is preferably halogen or a substituted or unsubstituted arylsulfonic acid residue, and is more preferably selected from the group consisting of chlorine, bromine, iodine and tosyloxy. R is a group corresponding to -continued

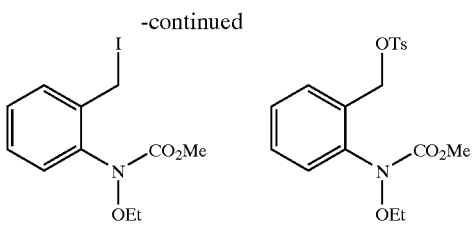

Ts is a p-toluenesulfonyl group.

Phosphorus compounds used in the present invention, which are added to facilitate reactions and actions to improve reaction selectivity, are preferably those substantially inactive to O-alkyllation reactions and with high affinity with various reaction reagents used in the present invention, for example, the said monovalent copper salts of pyrimidyloxy or pyridyloxy compounds. Phosphites have excellent properties in such characteristics and include lower alkyl phosphites such as trimethyl phosphite, triethyl phosphite, tri-n-butyl phosphite and others; or partially aryl substituted lower alkyl phosphites such as diphenylethyl phosphite and phenyldimethyl phosphite; or triaryl phosphites such as triphenyl phosphite; and further alkyl phosphines such as triethylphosphine, tributylphosphine, butyldiphenylphosphine and triphenylphosphine; arylphosphines and alkylarylphosphines. Phosphorus compounds to be added in this invention are suitably selected from the said organic phosphorus compounds. They are used alone, or two or more of them are mixed to use.

Amounts of phosphorus compounds mentioned above are not particularly restricted. An appropriate amount is used so that a reaction is carried out smoothly. It can be expected that an addition of 1 mol to 1 mol of a monovalent copper salt of alkylating agent preferably facilitates a desired reaction, and further a supplementary addition of up to about 1 mol favorably facilitates the reaction.

Solvents preferably used in the present invention include hydrocarbons such as hexane, octane and decane; and aromatic hydrocarbons such as benzene and toluene. These solvents can be also used when monovalent copper salts are produced. They are particularly advantageous to implement the methods of the present invention, because, in case of the preparation of copper salts by reactions with monovalent copper oxide, water produced from the reactions can be separated in turn to the bottom layer to remove so that monovalent copper salts of these compounds can be obtained with high purity and water removed without isolating them. In the present invention, in addition to the aforementioned solvents, ordinary organic solvents can be used, including ketones such as acetone, methyl ethyl ketone and methyl t-butyl ketone; ethers such as tetrahydrofuran, dimethyl ether and diethyl ether; esters such as ethyl acetate; aprotic polar solvents such as dimethyl sulfoxide and dimethyl furan; and alcohols such as methanol, ethanol and isopropanol. Amounts of solvents used are not particularly restricted. Amounts for carrying out reactions as homogeneous as possible may be used. It is not necessary to use more than required or appropriate. In equal-molar reactions amounts of solvents used are approximately 3.5 to 7 liters/Kg to the total weight (Kg) of starting materials added. A yardstick for a volume (liter) of solvents used for the reactions in the present invention is about 5 liters/Kg, an intermediate value of the above.

BEST FORMS TO IMPLEMENT THE INTENTION

The present invention is further described in detail in reference to Examples comparing with Comparative Examples. This invention is not restricted at all by these examples. "%" used in Examples and Comparative Examples is % by weight.

EXAMPLE 1

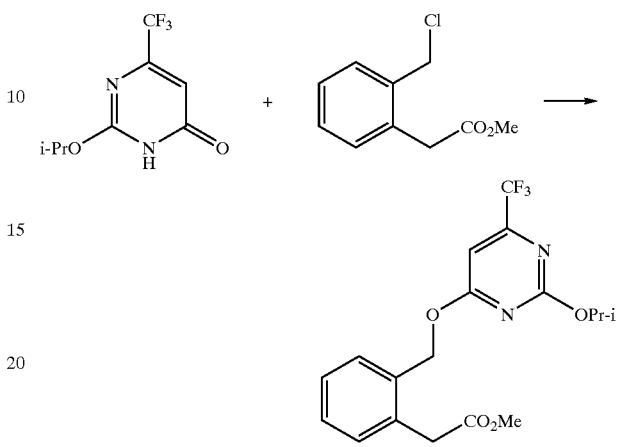

Preparation of methyl 2-(2-isopropoxy-6-trifluoromethylpyrimidin-4-yloxymethyl)phenyl acetate (Compound 1)

22.2 g of 2-isopropoxy-6-trifluoromethyl-4-hydroxypyrimidine and 7.2 g of copper(I) oxide were suspended in 200 ml of decane. The suspension was heated to 140° C. and kept at the same temperature until no water was recognized to form, while formed water was being taken into a quantitative water receiver. 16.6 g of triethyl phosphite was added, and, 20 minutes later, 19.9 g of methyl 2-chloromethylphenyl acetate was added at an instance. The reaction was carried out for 6 hours at 140 ~150° C., and then the resulting solution was left to stand over night at room temperature. An analysis of the reaction solution with high-performance liquid chromatography showed that the production rate of the target compound was 99% and a byproduct of methyl 2-(2-isopropoxy-6-trifluoromethylpyrimidin4-on-3-ylmethyl)phenyl acetate was produced less than 1%. 100 ml of water was added to the reaction solution. Deposited crystals were separated by filtration. The decane layer was separated and washed with 100 ml of 25% aqueous ammonia several times. The organic layer was washed with water and dried over magnesium sulfate.

Magnesium sulfate was separated by filtration. The obtained solution was kept at −20° C. to deposit crystals to give 18.4 g of the target compound as needle crystals. Its melting point was 55.0~55.5° C.

EXAMPLE 2

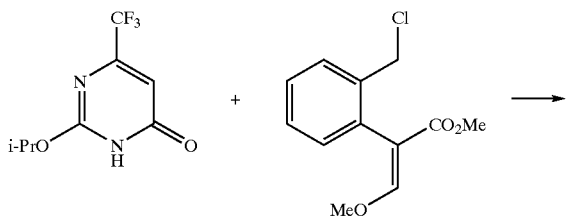

-continued

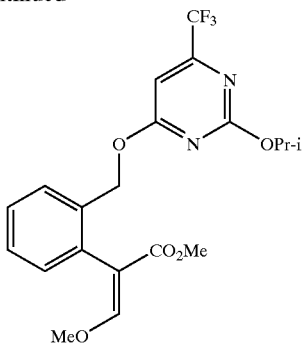

Preparation of methyl 3-methoxy-2-[2-(2-isopropoxy-6-trifluoromethylpyrimidin-4-yloxymethyl) phenyl]acrylate (Compound 2)

2.22 g of 2-isopropoxy-6-trifluoromethyl-4-hydroxypyrimidine and 0.72 g of copper(I) oxide were suspended in 50 ml of octane. The suspension was refluxed until no water was recognized to form, while formed water was being taken into a quantitative water receiver. 1.66 g of triethyl phosphite was added, and, 30 minutes later, 2.41 g of methyl 3-methoxy-2-(2-bromomethylphenyl)acrylate was added at an instance. The reaction was carried out for 20 hours at reflux of octane. The solution was cooled down to room temperature. 20 ml of acetone was added to it. Insoluble matter was filtrated, and further washed with 10 ml of acetone twice. The mixed solution of the obtained filtrate and washings was analyzed with high-performance liquid chromatography. Yields were 66.4% for the target compound, and as for byproducts 1.4% for methyl 3-methoxy-2-[2-(2-isopropoxy-6-trifluoromethylpyrimidin4-on-3-ylmethyl)phenyl]acrylate and 17.4% for 4-( α-methoxy)methylen-2H-chromen-3 (4H)-one.

EXAMPLE 3

Preparation of methyl 3-methoxy-2-[2-(2-isopropoxy-6-trifluoromethylpyrimidin-4-yloxymethyl)phenyl]acrylate (Compound 2)

2.22 g of 2-isopropoxy-6-trifluoromethyl-4-hydroxypyrimidine and 0.86 g of copper(I) oxide were suspended in 50 ml of octane. The suspension was refluxed until no water was recognized to form, while formed water was being taken into a quantitative water receiver. 1.86 g of triethyl phosphite was added, and, 30 minutes later, 3.65 g of methyl 3-methoxy-2-(2-bromomethylphenyl)acrylate was added at an instance. The reaction was carried out for 6 hours at reflux of octane. The solution was cooled down to room temperature. 20 ml of acetone was added to it. Insoluble matter was filtrated and washed with 10 ml of acetone twice. The mixed solution of the obtained filtrate and washings was analyzed with high-performance liquid chromatography. Yields were 82.1% for the target compound, and as for byproducts 3.1% for methyl 3-methoxy-2-[2-(2-isopropoxy-6-trifluoromethylpyrimidin4-on-3-ylmethyl)phenyl]acrylate and 14.8% for 4-(α-methoxy)methylen-2H-chromen-3(4H-one.

EXAMPLE 4

Preparation of methyl 3-methoxy-2-[2-(2-isopropoxy-6-trifluoromethylpyrimidin4-yloxymethyl)phenyl]acrylate (Compound 2)

2.22 g of 2-isopropoxy-6-trifluoromethyl-4-hydroxypyrimidine and 0.86 g of copper suboxide were suspended in 30 ml of octane. The suspension was refluxed until no water was recognized to form, while formed water was being taken into a quantitative water receiver. 1.86 g of triethyl phosphite was added, and, 30 minutes later, 3.65 g of methyl 3-methoxy-2-(2-bromomethylphenyl)acrylate was added at an instance. The reaction was carried out for 5 hours at reflux of octane. The solution was cooled down to 100° C. Hydrogen sulfide gas was blown into the solution at a rate of 15–30 ml/min for an hour. The resultant was stirred for 30 minutes. The formed precipitate was filtrated and washed with 9 ml of octane. The mixed solution of the obtained filtrate and washing was analyzed with high-performance liquid chromatography. The reaction yield was 72%. Octane was concentrated under reduced pressure. To the residue were added 10.3 ml of ethanol and 3.9 ml of water, and heated to 64° C. to dissolve. The resulting solution was left to cool over night. 2.8 ml of a mixed solution of ethanol/water (7/1) was added to it and cooled down to 5° C. to deposit crystals fully. The crystals were filtrated, washed with 1.4 ml of a mixed solution of ethanol/water (7/1) twice to give 2.46 g (yield 67%) of the target compound with melting point of 109~110° C.

EXAMPLE 5

Preparation of methyl 2-(2-isopropoxy-6-trifluoromethylpyrimidin-4-yloxymethyl)phenyl acetate (Compound 1)

111.1 g of 2-isopropoxy-6-trifluoromethyl-4-hydroxypyrimidine and 47.72 g of copper(I) oxide with 97.4% purity were suspended in 250 ml of chlorobenzene. The suspension was refluxed until no water was recognized to form, while formed water was being taken into a quantitative water receiver. The reaction solution was cooled down, and 124.94 g of triisopropyl phosphite was added at 100° C., followed by the addition of 109.26 g of methyl 2-chloromethylphenyl acetate. The reaction was carried out for 6.5 hours at 120° C. and then the solution was cooled down to room temperature. An analysis of the reaction solution with high-performance liquid chromatography showed that the reaction yield of the target compound was 86.6% and 3.5% for a byproduct of methyl 2-(2-isopropoxy-6-trifluoromethylpyrimidin-4-on-3 -ylmethyl)phenyl acetate.

Comparative Example 1

Comparative Example of Preparation of methyl 3-methoxy-2-[2-(2-isopropoxy-6-trifluoromethylpyrimidin4-yloxymethyl)phenyl] acrylate (Compound 2)

Into 73.8 g of a 23.3% DMF solution of methyl 3-methoxy-2-(2-bromomethylphenyl)acrylate were added in turn 6.2 g of potassium carbonate, 16.0 g of 2-isopropoxy-6-trifluoromethyl-4-hydroxypyrimidine and 60 ml of DMF. The suspension was reacted with stirring at 80° C. for an hour.

An analysis of the reaction solution with high-performance liquid chromatography showed that the reaction yield of the target compound was 62.4%, and as for byproducts 23.3% for methyl 3-methoxy-2-[2-(2-isopropoxy-6-trifluormethylpyrimidin4-on-3-ylmethyl)phenyl]acrylate and 5.2% for 4-(α-methoxy)methylen-2H-chromen-3(4H)-one.

The reaction solution was cooled down. Insoluble matter was filtrated. Then DMF was removed under reduced pressure. About 100 ml of an ethanol/water (7/1) solution was added to the residue and heated to dissolve to deposit crystals. 14.6 g of the target compound was obtained as granular crystals.

Comparative Example 2

Comparative Example of Preparation of methyl 3-methoxy-2-[2-(2-isopropoxy-6-trifluoromethylpyrimidin4-yloxymethyl)phenyl]acrylate (Compound 2)

3.04 g of potassium salt of 2-isopropoxy-6-trifluoromethyl-4-hydroxypyrimidine and 3.65 g of methyl 3-methoxy-2-(2-bromomethylphenyl)acrylate were suspended in 50 ml of octane. The resulting suspension was reacted at reflux of octane for 5 hours and cooled down to room temperature. 30 ml of ethyl acetate was added and insoluble matter was filtrated. The precipitate separated by filtration was washed with 20 ml of etyl acetate. A mixed solution of the obtained filtrate and washing was analyzed with high-performance liquid chromatography. The yield of the target compound was 13.3% and 75.0% for a byproduct of methyl 3-methoxy-2-[2-(2-isopropoxy-6-trifluoromethylpyrimidin-4-on-3 -ylmethyl)phenyl]acrylate.

Comparative Example 3

Comparative Example of Preparation of methyl 2-(2-isopropoxy-6-trifluoromethylpyrimidin-4-yloxymethyl)phenyl acetate (Compound 1)

1.33 g of 2-isopropoxy-6-trifluoromethyl-4-hydroxypyrimidine, 0.53 g of potassium carbonate and 0.99 g of methyl 2-chloromethylphenyl acetate were suspended in 12.5 ml of DMF. The suspension was heated to react at 80° C. for an hour. The reaction solution was poured into 50 ml of water and extracted with 100 ml of ethyl acetate. The organic layer was washed with 50 ml of water three times and dried over magnesium sulfate. An analysis of the ethyl-acetate solution with high-performance liquid chromatography showed that the production rate of the target compound was 41% and 59% for a byproduct of methyl 2-(2-isoporpoxy-6-trifluoromethylpyrimidin-4-on-3-ylmethyl)phenyl acetate.

Comparative Example 4

Comparative Example of Preparation of methyl 3-methoxy-2-[2-(2-isopropoxy-6-trifluoromethylpyrimidin-4-yloxymethyl)phenyl]acrylate (Compound 2)

2.22 g of 2-isopropoxy-6-trifluoromethyl-4-hydroxypyrimidine and 0.72 g of copper(I) oxide were suspended in 30 ml of toluene. The suspension was refluxed until no water was recognized to form, while formed water was being taken into a quantitative water receiver. 3.08 g of methyl 3-methoxy-2-(2-bromomethylphenyl)acrylate was added at an instance. The reaction was carried out for 5 hours at reflux of toluene. Then the solution was cooled down to room temperature. Insoluble matter was filtrated and further washed with 20 ml of acetone twice. The mixed solution of the obtained filtrate and washings was analyzed with high-performance liquid chromatography. The reaction yield was 22.3% and as for byproducts 0.7% for methyl 3-methoxy-2-[2-(2-isopropoxy-6-trifluoromethylpyrimidin-4-on-3-yloxymethyl)phenyl]acrylate and 77% for 4-(α-methoxy) methylen-2H-chromen-3(4H)-one.

APPLICABILITY IN INDUSTRIES

Chain or cyclic compounds having one or more CONH groups or enol structures thereof in the molecules, which are starting materials of the present invention, such as pyrimidone and pyridone compounds, have oxygen and nitrogen atoms as active sites for alkylation reactions. According to the methods of this invention, alkylation reactions proceed at the said oxygen-atom sites highly selectively, and products from O-alkylation reactions are obtained in high yields. Therefore, with the preparation methods of the present invention, a wide range of pyrimidyloxy derivatives and pyridyloxy derivatives useful as intermediates for agrochemicals and medicines can be produced efficiently in high yields with economic advantage.

What is claimed is:

1. A selective O-alkyllation method comprising an O-alkylation reaction of a chain or cyclic compound having one or more structures represented by Formula (I)

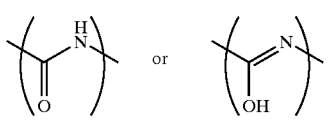

as partial structures, with Compound RL having a leaving group (wherein R is optionally substituted alkyl, optionally substituted allyl or optionally substituted aralkyl; and L is a leaving group), a monovalent copper salt derived from the said chain or cyclic compound is reacted in the presence of a phosphorus compound represented by Formula (II)

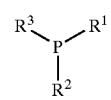

(wherein $R^1$, $R^2$ and $R^3$ are, each same or different, hydrogen, alkyl, aryl, aralkyl, alkoxy, aryloxy or aralkyloxy with the proviso that $R^1$, $R^2$, and $R^3$ are not all hydrogen).

2. A selective O-alkylation method according to claim 1, in which the cyclic compound having one or more structures represented by Formula (I) as partial structures is a pyrimidone, pyridone or triazine compound represented by Formula (III)

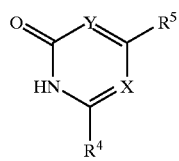

(wherein X and Y are each independently CH or N; $R^4$ is hydrogen, lower alkyl, haloalkyl or lower alkoxy; and $R^5$ is hydrogen, lower alkyl or trifluoromethyl).

3. A selective O-alkyllation method according to claim 1, in which the compound having a leaving group is a compound represented by Formula (IV)

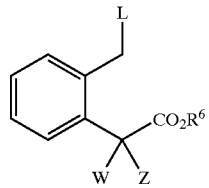

(wherein L is a leaving group; $R^6$ is lower alkyl; and W and Z are both hydrogen or become one to form =O, =NOCH$_3$, =CHOCH$_3$), or by Formula (V)

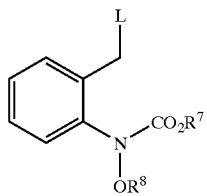

(wherein, $R^7$ and $R^8$ are, same or different, chain or branched lower alkyl, haloalkyl, cycloalkyl or aralkyl; and L is as defined above).

4. A selective O-alkyllation method according to claim 2, in which Formula (III) is

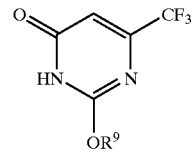

(wherein $R^9$ is lower alkyl).

* * * * *